United States Patent [19]

Platzer

[11] Patent Number: 5,728,586

[45] Date of Patent: Mar. 17, 1998

[54] PHOTOIONIZATION DETECTOR AND PROCESS

[75] Inventor: Bernhard Platzer, Cassano d'Adda, Italy

[73] Assignee: Fisons Instruments S.p.A., Milan, Italy

[21] Appl. No.: 617,826

[22] PCT Filed: Jul. 15, 1994

[86] PCT No.: PCT/IT94/00114

§ 371 Date: Mar. 14, 1996

§ 102(e) Date: Mar. 14, 1996

[87] PCT Pub. No.: WO96/02834

PCT Pub. Date: Feb. 1, 1996

[51] Int. Cl.[6] .................... G01N 30/64; G01N 21/00
[52] U.S. Cl. .................... 436/153; 436/149; 436/161; 422/83; 422/91; 422/98; 422/89; 73/23.35; 73/23.4
[58] Field of Search .................... 422/83, 89, 98, 422/54, 90, 91; 436/147, 149, 153, 154, 161, 181; 73/23.2, 23.22, 23.26, 23.35, 23.4, 23.42, 864.82, 864.83

[56] References Cited

U.S. PATENT DOCUMENTS

| 4,137,750 | 2/1979 | French et al. | 73/23 |
| 4,804,846 | 2/1989 | Hall | 250/379 |
| 5,561,344 | 10/1996 | Hsi | 313/494 |
| 5,578,271 | 11/1996 | Simon et al. | 422/98 |

Primary Examiner—Long V. Le
Attorney, Agent, or Firm—Millen, White, Zelano, & Branigan, P.C.

[57] ABSTRACT

A photoionization detector for a gaschromatographic apparatus includes an ionization chamber provided with a polarizing electrode and a collector electrode. The electrodes are mounted on and heated by a base portion of the detector. A lamp with a window spaced from the chamber and mounted on the base portion through supporting means having low thermal conductivity is provided. A gas curtain of a gas that is transparent to the said lamp radiation is provided at least between the window and the ionization chamber and comprises a first portion of substantially still gas acting as thermal insulant and a second portion of flowing gas also acting as sweep gas for the lamp window.

24 Claims, 5 Drawing Sheets

PHOTOIONIZATION DETECTOR AND PROCESS

TECHNICAL FIELD

The present invention relates to a photoionization detector and to a process of detecting effluents from a gaschromatographic column in photoionization mode.

BACKGROUND ART

Photoionization detectors (PIDs) are known in the art and are generally used to detect gaschromatograph eluates. Basically, these detectors use the radiant energy generated by a UV lamp to ionize at least part of the compounds eluting from the GC column. Ionization is carried out in an ionization chamber containing two electrodes, anode and cathode, acting as ion accelerator and collector, and a window, sealed to the lamp, through which the lamp radiation passes into the ionization chamber.

Present PIDs have several drawbacks, resulting from the basic requirements of a PID, i.e. that the lamp window and ion chamber must be as close as possible, to have high irradiance and good ionization of the effluents, and that the lamp and ionization chamber must be heated to avoid condensation of the effluents exiting the GC column. The main drawback is due to the fact that heating of the detector base body to temperatures of up to 350°–400° C., i.e. typical detector temperatures, results in shortened lamp lifetime due to deterioration of the seal between the lamp body and the lamp window. Furthermore, the lamp has to be sealed against the detector; this is usually done with a polymeric gasket or O-ring between the lamp window and the detector body. At high temperatures this polymer seal releases compounds which then deposit onto the window, decreasing lamp output.

This means that, because of the above cited requirement of closeness of the window to the detector base body, actual operating maximum temperature of the detector is about 250°–280° C., in order to avoid cited problems. This temperature limitation results in the possibility of analyzing volatile compounds only. High boiling compounds, i.e. those that require a detector temperature of up to 400° C., cannot be analyzed in the PID mode—if state of the art PID detectors are used.

Another drawback is that the sample stream contacting the lamp window results in window fogging because of polymerization of the sample compounds by UV radiation: the window must therefore be periodically cleaned—or replaced.

A further drawback of the known PIDs is that many compounds eluting from the column, upon contact with metal electrodes are partially decomposed and are therefore lost for analysis by a further detector located downstream the PID, such as e.g. a Flame Ionization Detector (FID).

German patent DD-A-290296 discloses a photoionization detector having electrodes that are transversal to GC column and wherein the window is replaced by a light-guiding element of magnesium fluoride. This embodiment has the same problems above cited, in that the gaskets release some material and deposition of material on the light-guiding element occurs.

U.S. Pat. No. 4,804,846 discloses a PID provided with a duct feeding a purge gas to the ionization chamber space adjacent to the window of the hot lamp, in order to fluidically sweep away the sample compounds that could contact the lamp window, to thus try to prevent its fouling by polymerization of sample compounds under UV radiation action. Anyway, material released from the lamp gasket may (and does) easily deposit onto the lamp window. In this embodiment, the ionization chamber volume is as small as possible to reduce dead volume, the sweep gas exits the chamber through an exit transfer tube, and the electrodes are housed in recesses of a doubly conical polyimide seal. The presence of this seal results in above cited problems of thermal decomposition of the seal and consequent high baseline current during analyses at elevated temperature.

More recently (Pittcon '94—Chicago) Wentworth et al. disclosed a windowless PID, namely a Pulsed Discharge Photoionization Detector—see Abstracts of the Pittsburg Conference, n. 660. This completely different solution results in some limitations if compared to classic PIDs with sealed UV lamps and chambers, e.g because of their reduced selectivity.

DISCLOSURE OF THE INVENTION

It is one object of this invention to solve the above cited problems by means of an improved photoionization detector in which the detector base could be held at a temperature of up to 400° C. without stressing the seal between the lamp and the window.

It is another object of the invention to provide a PID that is adapted to be serially connected to a further detector.

It is another object of the invention to provide a PID in which fouling of the lamp window is avoided, whilst having at the same time a good irradiance and ionization of the effluents within the ionization chamber of the lamp.

It is a further object of the invention to provide a method of carrying out photoionization detection that is suitable also for high boiling compounds and that does not result in shortened lamp life nor in high baseline current at elevated temperatures.

These objects are met through the present invention, that provides a photoionization detector wherein the lamp is held at low temperature, whilst the detector base is held at elevated temperature, that is characterized according to claim 1.

The invention also provides a process of photoionization detection characterized according to claim 9.

The unforeseeable existence of a very steep temperature gradient between the lamp and the detector base, as obtainable through the combined use of low thermal conductivity elements and of a gas curtain in front of the lamp window, results in many advantages to the state of the art.

In fact, it is possible to operate the detector base over the whole temperature range usually adopted in gaschromatographic analyses, i.e. any compound that can be analysed by GC can be detected, while still having a window temperature of about 80°–100° C. Furthermore, any sealing gaskets and electric connecting elements present in the detector are held at low temperature: their deterioration and the release of thermally decomposed material therefrom are avoided.

A further advantage is that the gas curtain also acts as sweep gas and keeps cleaner the window.

Finally, the specific location of the exit of the GC column, or transfer tube, and of the gases exit conduit is such that any unrequired contact between the compounds present in the effluent and the metal electrodes is avoided: the gases leaving the ionization chamber may thus be used for detection by additional detectors serially connected to the PID.

BEST MODE FOR CARRYING OUT THE INVENTION

The invention will now be further disclosed with reference to the enclosed non-limiting drawings, in which.

Figure 1:
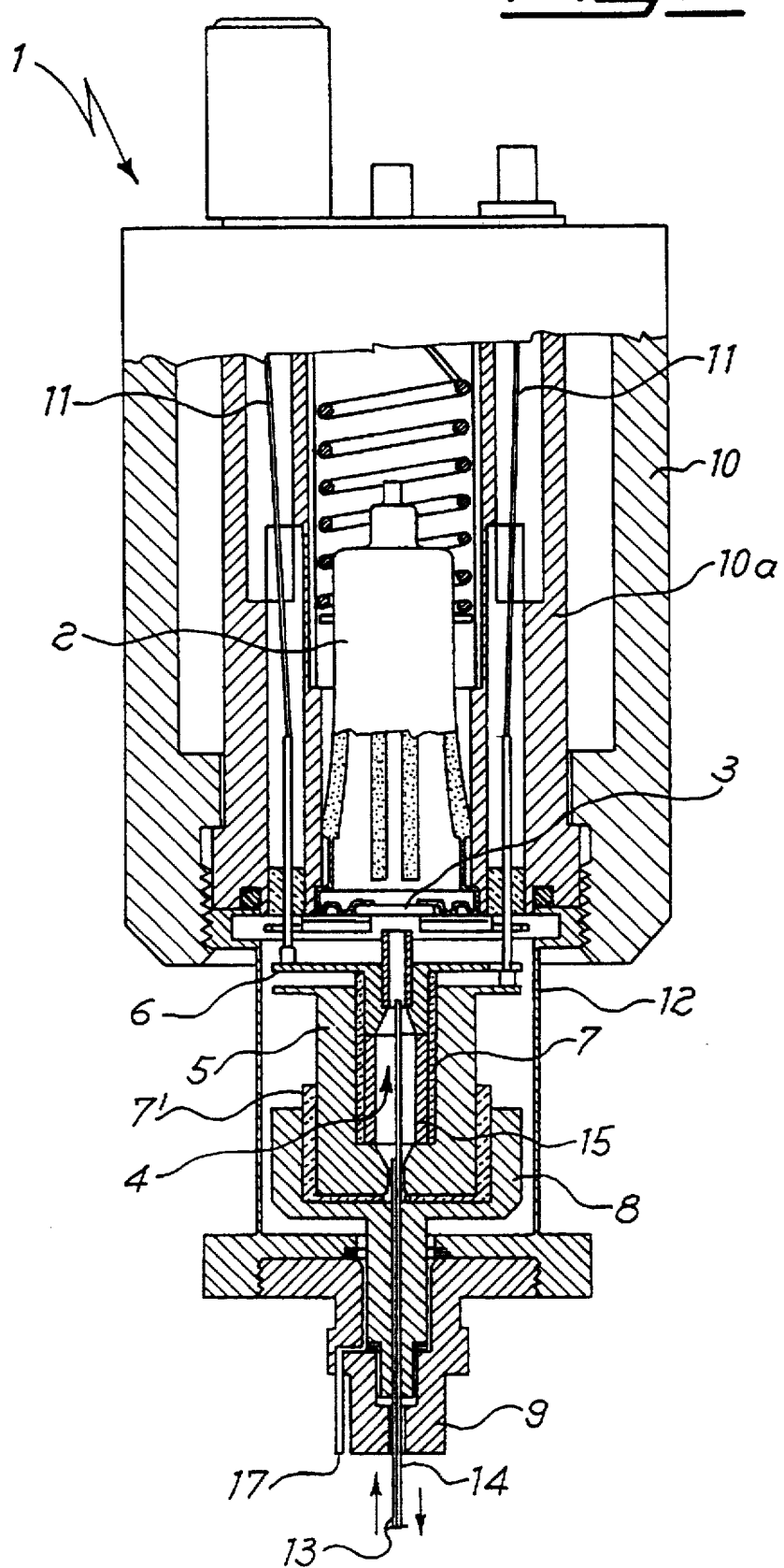
FIG. 1 is a sectional view of a first embodiment of the invention.
Figure 2:
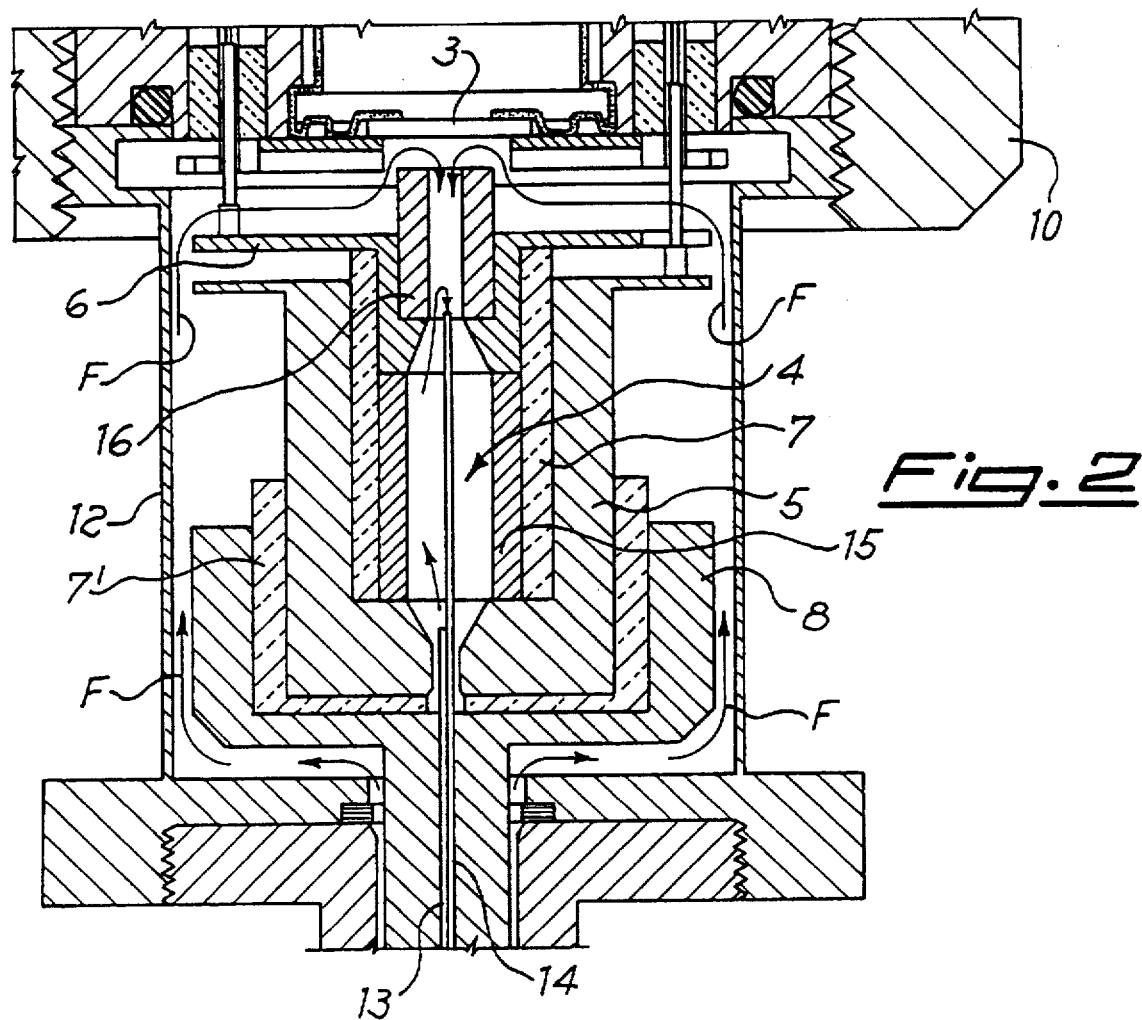
FIG. 2 is an enlarged view of the embodiment of FIG. 1.
Figure 3:
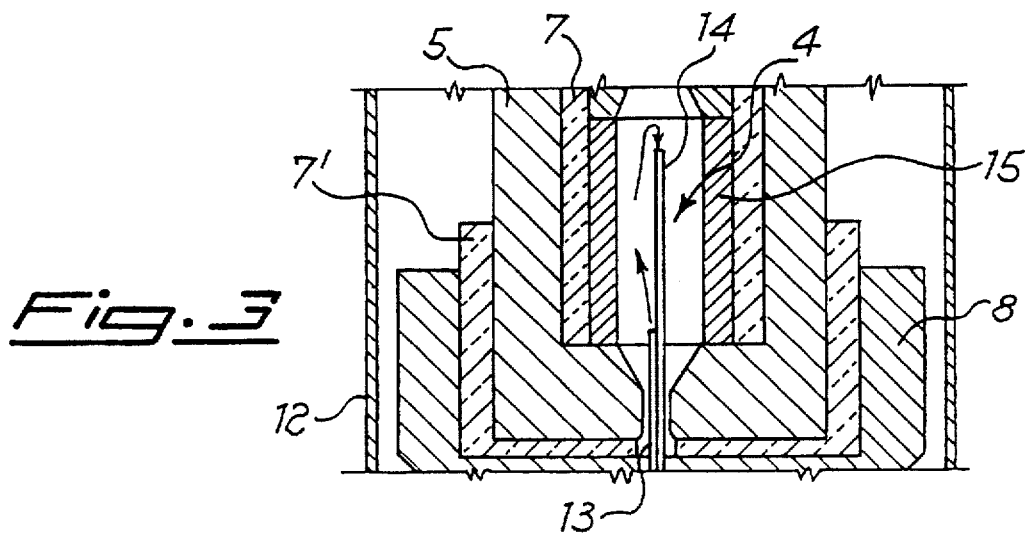
FIG. 3 is a partial view of the embodiment of FIG. 2 with a different location of inlet and exit tubes.
Figure 4:
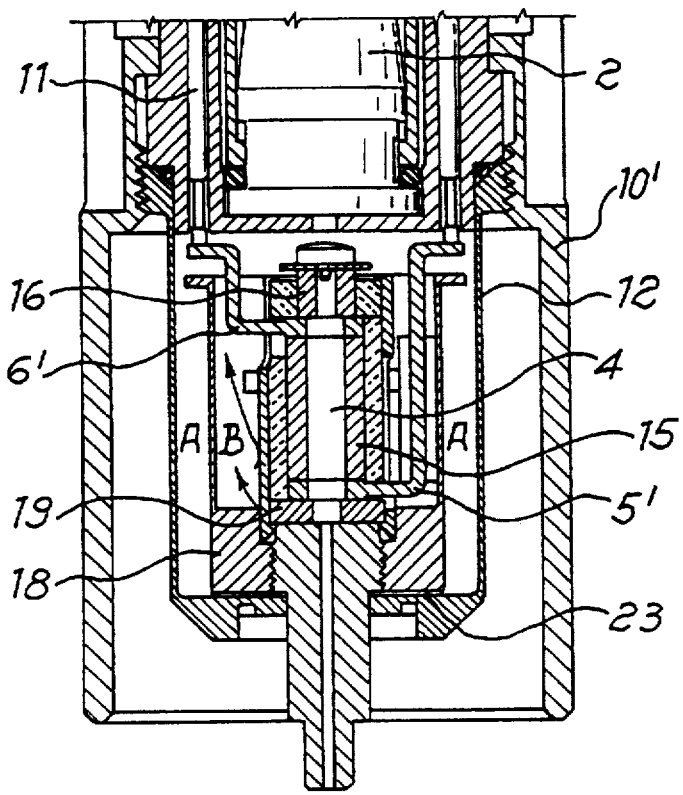
FIG. 4 is a sectional view of another embodiment of the invention.
Figure 5:
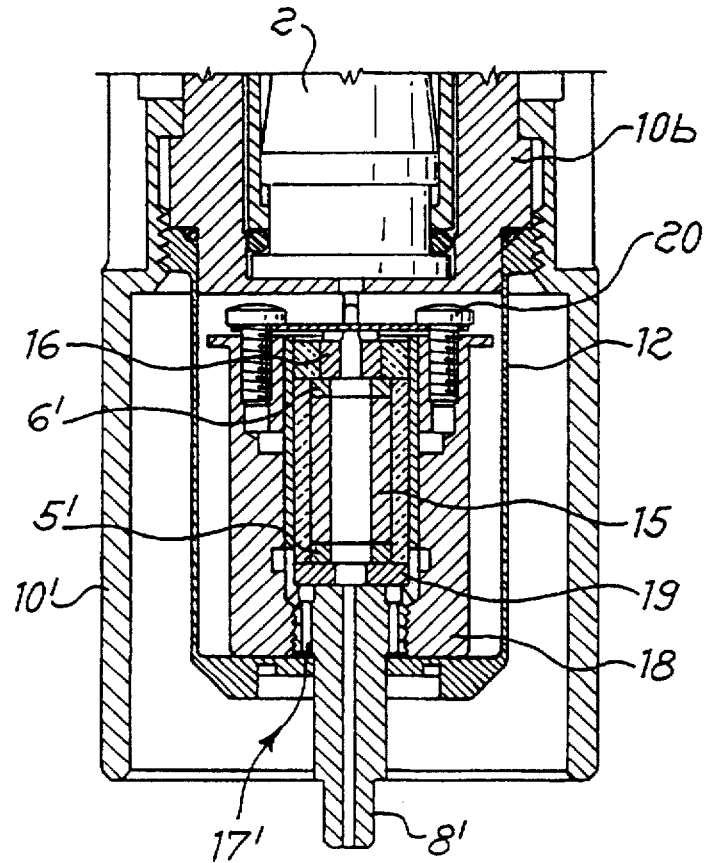
FIG. 5 is a sectional view, rotated by 90°, of the embodiment of FIG. 4.
Figure 7:
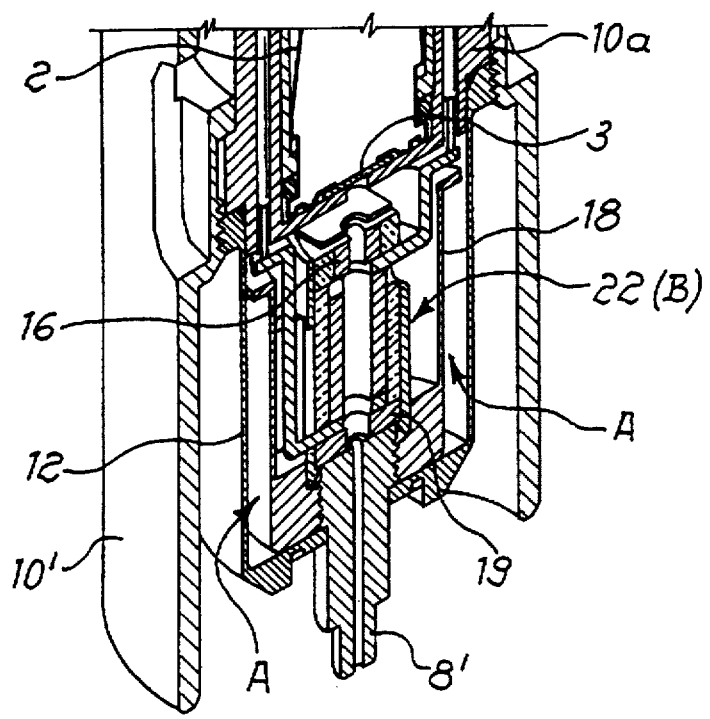
FIG. 7 is a perspective and fully sectional view of the embodiment of FIG. 6.
Figure 6:
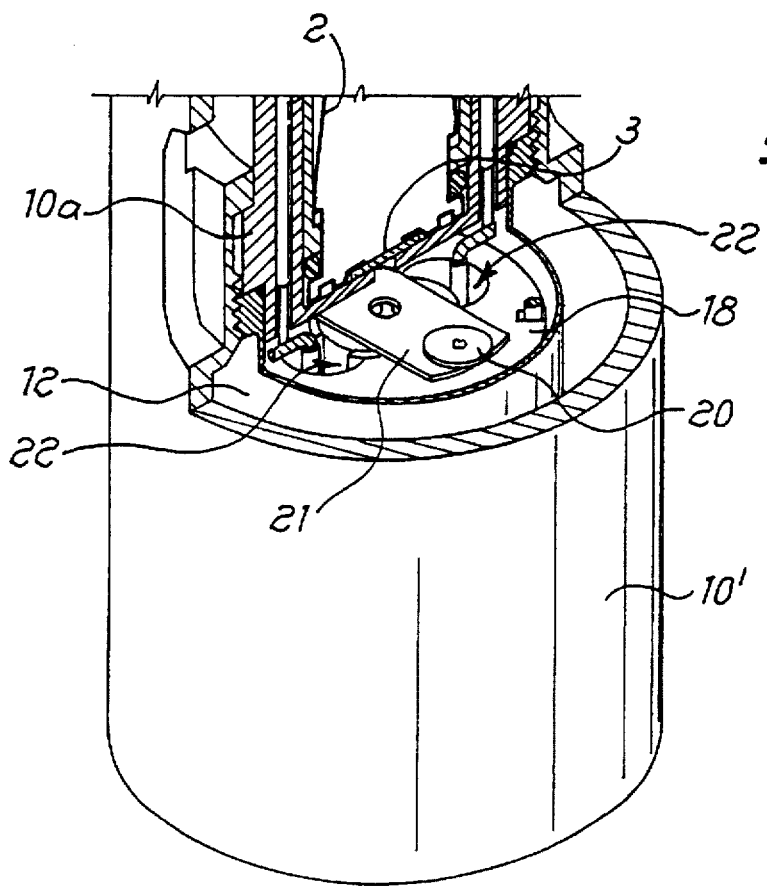
FIG. 6 is a partially sectional and perspective view corresponding to the view of FIG. 4.

Detector 1 of FIGS. 1 to 3 comprises a lamp 2 that is provided with a window 3 through which is passed the ionizing radiation generated by the lamp. Window 3 is axially aligned to ionization chamber 4 that is formed between two electrodes (anode and cathode) that act in a known way as polarizing electrode 5 and collector electrode 6. The chamber 4 is provided with inlet tube 13 for feeding to the chamber the effluents of the GC column. Inlet means 13 may be the actual column end portion or a transfer tube connected to the end of said column. Exit tube 14 is also provided to discharge the effluents from chamber 4 to the ambient or for feeding them to a further detector, e.g of the FID type.

In the embodiment shown in FIGS. 1-3, electrodes 5 and 6 are cylindrical and are mounted concentric to each other; this means that collector electrode 6 is partially housed within polarizing electrode 5, from which it is spaced by an inert, inorganic, element 7 that acts as electric insulating means. Lower electrode 5 is mounted through an insulating element 7 and a bracket 8, or similar supporting element, onto a base element 9. Base element 9 is heatable and electrodes 5 and 6 are in thermal exchange with base 9 and are thus heated at its temperature. i.e. at a temperature that is equal or higher than the elution temperature of said compounds.

The lamp 2 is housed in element 10a that also houses the electric hardware relevant to lamp 2 and electric contacts 11 relevant to electrodes 5 and 6; these contacts are advantageously forced against electrodes 5 and 6 by springs, in a way known per se in the art. Housing element 10a is provided with a heat dissipating structure 10, e.g. in Aluminium or equivalent metal, and is mounted, e.g. screwed, on supporting means 12. Means 12 is a hollow cylinder made of a material having low thermal conductivity. With "material having a low thermal conductivity" is here meant stainless steel or any equivalent material that has thermal conductivity as low as possible to thermally insulate, as far as possible, elements 10a and 10 from base body 9. Supporting means 12 houses, without contacting them, ionization chamber 4 and electrodes 5 and 6, and is mounted onto base element 9. However, the heat transfer to element 10a and lamp 2 is very low, due to the design of means 12; namely, the use of stainless steel with wall thickness of 0.4 to 0.6 mm will be preferred.

As shown in FIGS. 1-3, the pneumatic sealing of window 3 is essentially obtained by means of a curtain of inert gas that flows along window 3 and the interface portion between elements 10a and 12, and from there to exit tube 14. A preferred gas is nitrogen.

In FIG. 2 references F show the path of inert gas, from feeding tube 17 (FIG. 1) to the bottom of supporting means 12, then upwards along its walls to window 3 and from there to ionization chamber 4. Thus, the inert gas that gives pneumatic and thermal insulation to the lamp and window assembly, also acts as sweeping gas for window 3, confining effluents from GC column within chamber 4. Moreover, the gas curtain and flow prevents leakage of ambient air into ionization chamber without using any polymeric seal for chamber 4 (i.e. in the hot portion of the detector): thus, no release of contaminants occurs, even at high temperatures.

The combined use of thermally insulating supporting means 12 and of a gas curtain results in a detector wherein the temperature of the base body 9 (and of the ionization chamber 4 that is in thermal exchange therewith) is about 350°–400° C., and the temperature of lamp 2 and window 3 is about 80° C. and not higher than 100° C.

Preferred inlet and outlet means to and from the chamber 4 according to the invention are capillary columns 13 and 14 or equivalent means. Namely, column 13 is corresponding to inlet means for gaseous compounds to be detected and may be the actual GC column or a transfer tube connected to the GC column. The exit end of column 13 is located near electrode 5 of chamber 4, in order to have the longest possible path of the effluents within chamber 4 and therefore the greatest possibility of their ionization by the radiation from lamp 2.

For this purpose, the length of ionization chamber 4 is preferably within the range from 8 to 20 mm, and usually of about 15 mm. This feature is contrary to the teaching of the state of the art, according to which the ionization chamber volume should be as small as possible.

Exit tube 14 has an inner diameter that is typically greater than (or equal to) that of tube 13, in order to have a smaller pneumatic resistance than that of inlet tube 13. The end of tube 14, is advantageously located at the upper end of chamber 4, i.e. near collector electrode 6. In any case, the end of exit tube 14 is spaced from window 3 and is downstream to it with respect to the gas flow F. In the preferred embodiment of FIG. 3, the ends of tubes 13 and 14 are less spaced from each other than in the embodiment of FIG. 2, and both are located well within chamber 4, spaced from electrodes. Chamber 4 is preferably made of an inert and insulating material such as quartz, sapphire or similar material that may be used as a liner 15. It is thus possible to avoid any contact between the non-ionized gaseous effluents and the electrodes in order to avoid their decomposition or adsorption and to send them to a further detector.

Between chamber 4 and window 3 an element, 16, is provided for transmitting to chamber 4 the radiation generated by lamp 2. Such element is preferably a tube 16 of inert material, e.g. quartz or metal, and has smooth inner walls to reflect the radiation into chamber 4 with minimum energy loss.

The preferred embodiment of FIGS. 4 to 7 is substantially the same as the previously disclosed ones. In these figures the same elements have retained the same reference number.

The main differences are that the electrodes are simply spaced, being no more concentric, and that ionization chamber 4 is housed within element 18, made of thermally conductive material, e.g. brass, that is heated by the base body 9 (not shown in FIGS. 4–7, but identical to that disclosed in FIGS. 1–3). Element 18 has a full bottom portion and is provided with two conduits 22 housing the connecting portions of electrodes 5' and 6' and forming a path along which inert gas is fed to be maintained at a temperature that is substantially the same as that of the chamber 4. This first path is referred to with B in FIG. 4. The closed bottom of conduits 22 (FIGS. 6 and 7) is connected to inlet port 17' (FIG. 5) to which inert gas is fed. The upper side of conduits 22 is spaced from window 3, in order to connect them to the space between element 18 and supporting means 12, referred to with letter A in FIG. 4, and to enable the gas curtain or sheath to flow along window 3. The gas in this portion is substantially still, and this may result in the gas becoming polluted, even if only after a long time. To avoid this, one or more small grooves 23 may be provided in the bottom portion of the element 18, to put into communication spaces A and B and thus provide a small "purge" flow of inert gas.

In any case, the actual result of the embodiment according to FIGS. 4–7 is that the gas curtain is formed by a first portion of substantially still gas, in space A and immediately adjacent to window 3, and by a second portion of flowing gas acting as sweep gas for the lamp window. It should be noted that by "sweep gas" is here meant that the gas flow confines the effluents into the ionization chamber 4.

In this preferred embodiment, two screws 20 are provided on the top of element 18 to cooperate with a plate 21 in order to hold in place the radiation transmitting tube 16, electrode 6', liner 15 of chamber 4, electrode 5' and a base ring 19 that acts as seat for electrode 5'. Ring 19 is of quartz or other equivalent insulating material. Two conduits or grooves may be provided under plate 21 to facilitate passage of inert gas under plate 21 to tube 16 and chamber 4.

The process according to the invention provides that the gaseous compounds that have been separated by the GC column and are the effluents from said column are fed through tube 13 to ionization chamber 4, which is held essentially at the same temperature as base body 9 of detector 1, i.e. at a temperature of up to 370°–400° C. A flow of gas is fed to the space along the walls of supporting means 12, and window 2, into tube 16 and ion chamber 4. In the preferred embodiment, the gas flow splits into a portion of substantially still gas, or with a very reduced flow rate (i.e. the purse flow through grooves 23), and in a portion of gas flowing to confine the effluents within the ionization chamber and have them leave said chamber through exit tube 14.

A part of the incoming effluents is ionized by the radiation generated by lamp 2 and transmitted to chamber 4 through reflecting tube 16. The ionized compounds are then detected by electrodes 5 and 6 (or 5' and 6') and the portion of compounds that was not ionized is conducted through tube 14, e.g. to a further FID detector.

Figure 8:
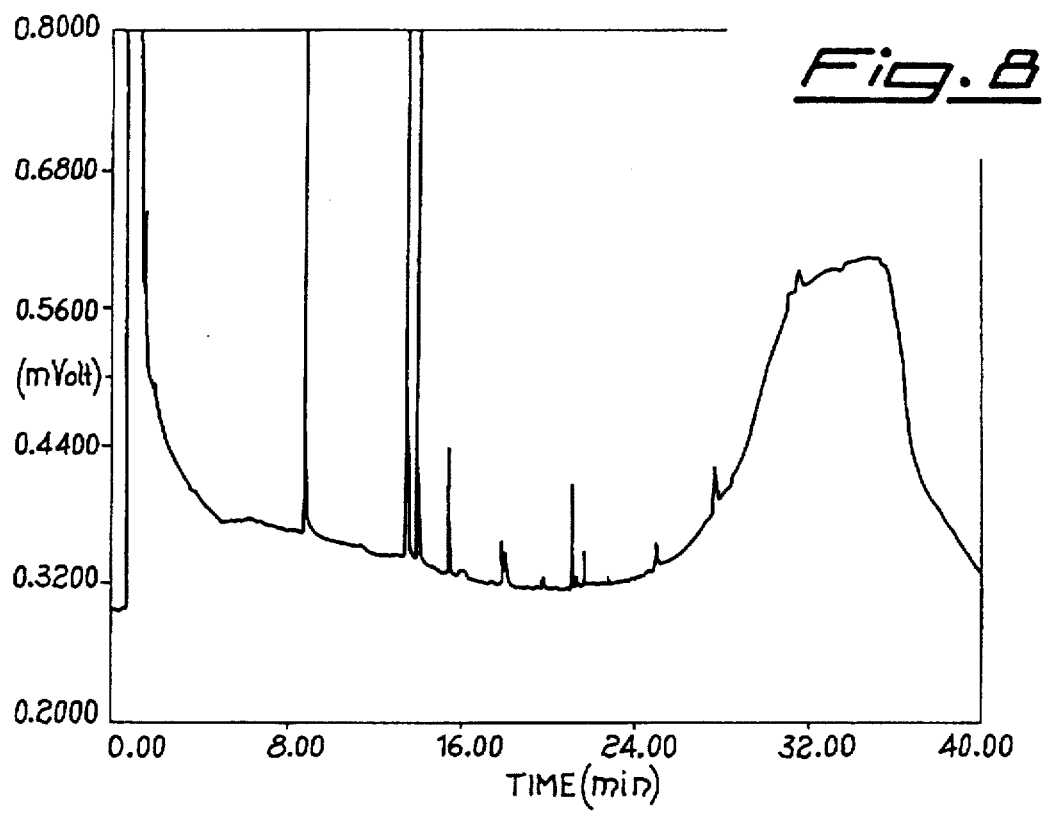
FIGS. 8 and 9 are chromatograms of GC analyses using a FID (FIG. 8) and a PID according to the invention (FIG. 9).
Figure 9:
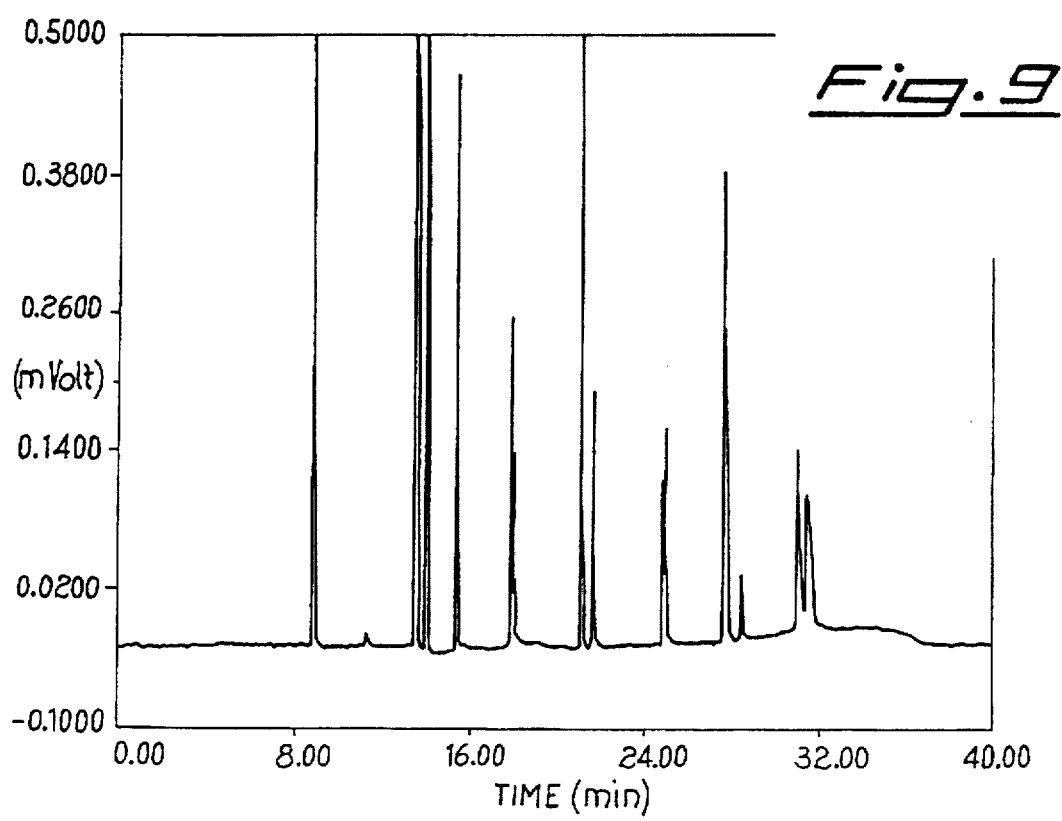

FIGS. 8 and 9 show two chromatograms resulting from GC analysis of a mixture containing high boiling compounds, namely Polynucler Aromatic Hydrocarbons Mixture 610-M by SUPELCO Inc. (Catalog No. 4-8743).

In this analysis the PID detector base was heated to 370° C. and elution temperature was from 80° to 330° C. Lamp energy was 8.4 eV.

FIG. 9 shows a chromatogram obtained with a PID detector according to this invention. FIG. 8 refers to the detection by means of a Flame Ionization Detector of the non-ionized compounds conducted from the PID to the FID. From these figures it is apparent the better response of high boiling compounds in the PID mode analysis with respect to the FID mode; it should also be stressed that the smaller peaks correspond to about 170 picograms of each compound detected by the PID and FID detectors.

I claim:

1. A photoionization detector for a gaschromatographic apparatus, comprising:

a lamp (2) aligned with a window (3) for emitting radiation that passes through the window (3); and an ionization chamber (4) provided with a polarizing electrode (5, 5') and a collector electrode (6, 6');

said ionization chamber (4) being mounted on an insulating element (7) on a base portion (9) of the detector and being heated by the base portion (9); said lamp (2) being spaced from said ionization chamber (4) and being mounted on said base portion (9) by a support (12) which thermally isolates the lamp (2) from the ionization chamber (4), and a gas curtain of a gas transparent to the said lamp radiation being provided between said window (3) and said ionization chamber (4) to provide a pneumatic seal for preventing leakage of ambient air past the non-polymeric element and into the ionization chamber (4) without using a gasket.

2. A detector according to claim 1, wherein said gas curtain is comprising a first portion (A) of substantially still gas disused within an outer annular chamber and acting as thermal insulant and a second portion (B) of flowing gas flowing in an inner annular chamber when also acting as sweep gas for said lamp window (3).

3. A detector according to claim 1, wherein a radiation reflecting hollow element is located between said ionization chamber (4) and said lamp window (3).

4. A detector according to claim 1, wherein inlet (13) and exit (14) tubes for feeding and exiting gas to and from said ionization chamber are provided, said tubes having different resistances and spaced ends.

5. A detector according to claim 4, wherein said tube ends are both located within the ionization chamber (4) and are spaced from said electrodes (5, 6; 5', 6').

6. A detector according to claim 1, wherein said ionization chamber (4) is located within thermally conducting housing means (18) located between said chamber (4) and said support (12) and spaced therefrom.

7. A detector according to claim 1, wherein the distance between polarizing electrode and collecting electrode is within the range from 8 to 20 mm.

8. A detector according to claim 1, wherein the ionization chamber (4) is made of or has an internal surface of sapphire or quartz.

9. A detector according to claim 1, wherein said gas curtain is nitrogen.

10. A process of detecting gaseous effluents from a gaschromatographic column by means of a detector apparatus, comprising a lamp (2) aligned with a window (3) for emitting radiation which passes through the window, and an ionization chamber (4) provided with a polarizing electrode (5,5') and a collector electrode (6,6'); said ionization chamber (4) being mounted on and heated by a base portion of the detector; said lamp (2) is spaced from said chamber (4) and is mounted on said base portion by a support (12) which thermally isolates the lamp (2) from the ionization chamber (4), the process comprising the following steps:

feeding the gaseous effluents exiting from said column to the ionization chamber (4);

heating said ionization chamber (4) to such a temperature that said effluents are maintained in a gaseous condition;

generating an ionizing radiation by the lamp (2) and sending said radiation to the ionization chamber (4) through the window (3);

providing a gas curtain of an inert gas that is substantially transparent to said lamp radiation at least between said ionization chamber (4) and said window to thermally and pneumatically insulate said lamp (2) and said window (3) from the heated ionization chamber (4); and sealing the ionization chamber from the ambient air without using a gasket by flowing the gas through the ionization chamber.

11. A process according to claim 10, wherein an inert gas flow is fed to said detector apparatus and is divided into a gas curtain portion (A) having no flow or a reduced flow and into a gas curtain portion (B) comprising a gas flow having a higher flow than said reduced flow, confining said gaseous effluents within said ionization chamber (4) and removing said effluents from said chamber (4) through an exit tube (14).

12. A process according to claim 10, wherein said radiation is sent to said ionization chamber (4) through a radiation reflecting tube (16).

13. A process according to claim 11, wherein said gas flow is flowed through a heated path (B) to heat said gas before it is fed to the ionization chamber (4).

14. A process according to claim 10, wherein said effluents leaving the ionization chamber (4) are conducted to a further detection by a supplemental detector.

15. A process according to claim 11, wherein said radiation is sent to said ionization chamber (4) through a radiation reflecting tube (16).

16. A process according to claim 11, wherein said gas flow is flowed through a heated path (B) to heat said gas before it is fed to the ionization chamber (4).

17. A process according to claim 15, wherein said gas flow is flowed through a heated path (B) to heat said gas before it is fed to the ionization chamber (4).

18. A process according to claim 11, wherein said gas curtain consists essentially of nitrogen.

19. The photoionization detector of claim 1, wherein the polarizing electrode (5,5') is spaced from the collector electrode (6,6') by an inert, inorganic electrical insulator (7) and the polarizing electrode (5,5') is separated from a mount (8) thereof with said insulating element (7') to provide a gasketless mounting whereby deposits on the window (3) due to decomposition of seal material are avoided.

20. The photoionization detector of claim 19, wherein the mount (8) is mounted on the base (9) and wherein the base (9) is heated to heat the ionization chamber (4).

21. The photoionization detector of claim 20, wherein the support (12) for the lamp (2) is mounted on the base (9) and is comprised of an annular cylindrical portion (12a) which is radially spaced from the ionization chamber (4) and is joined to a relatively high heat dissipating structure (10) surround the lamp (2).

22. The photoionization chamber of claim 21, wherein the support (12) is made of stainless steel and the heat dissipating structure is made of aluminum.

23. The photoionization chamber of claim 1, wherein the support (12) is made of aluminum.

24. The photoionization chamber of claim 1, wherein the inert gas is nitrogen.

* * * * *